US008900250B2

(12) United States Patent
Fritscher-Ravens et al.

(10) Patent No.: US 8,900,250 B2
(45) Date of Patent: Dec. 2, 2014

(54) APPARATUS AND METHODS FOR REMOVING LYMPH NODES OR ANCHORING INTO TISSUE DURING A TRANSLUMENAL PROCEDURE

(75) Inventors: Annette Fritscher-Ravens, Bruchhausen-Vilsen (DE); Vihar C. Surti, Winston-Salem, NC (US)

(73) Assignee: Cook Medical Technologies, LLC, Bloomington, IN (US)

( * ) Notice: Subject to any disclaimer, the term of this patent is extended or adjusted under 35 U.S.C. 154(b) by 0 days.

(21) Appl. No.: 12/543,000

(22) Filed: Aug. 18, 2009

(65) Prior Publication Data
US 2010/0049208 A1 Feb. 25, 2010

Related U.S. Application Data

(60) Provisional application No. 61/090,115, filed on Aug. 19, 2008.

(51) Int. Cl.
| | |
|---|---|
| *A61B 17/26* | (2006.01) |
| *A61B 10/04* | (2006.01) |
| *A61B 17/221* | (2006.01) |
| *A61B 10/02* | (2006.01) |
| *A61B 19/00* | (2006.01) |
| *A61B 17/00* | (2006.01) |

(52) U.S. Cl.
CPC ......... *A61B 10/04* (2013.01); *A61B 2017/2215* (2013.01); *A61B 10/0266* (2013.01); *A61B 2019/5425* (2013.01); *A61B 2017/00867* (2013.01); *A61B 2019/547* (2013.01)
USPC ...................................................... 606/110

(58) Field of Classification Search
USPC .................. 606/106, 110, 113, 114, 127, 200
See application file for complete search history.

(56) References Cited

U.S. PATENT DOCUMENTS

| | | | |
|---|---|---|---|
| 2,199,025 | A | 4/1940 | Conn |
| 2,671,444 | A | 3/1954 | Pease, Jr. |
| 3,209,422 | A | 10/1965 | Dritz |

(Continued)

FOREIGN PATENT DOCUMENTS

| | | |
|---|---|---|
| EP | 0310582 A1 | 4/1989 |
| EP | 0774237 A2 | 5/1997 |

(Continued)

OTHER PUBLICATIONS

Office Action for Japanese Patent Application 2011-523934 dated Aug. 27, 2013, 7 pgs Including English translation.

(Continued)

*Primary Examiner* — Ashley Fishback
(74) *Attorney, Agent, or Firm* — Brinks Gilson & Lione

(57) ABSTRACT

The present embodiments provide apparatus and methods suitable for removing lymph nodes or providing a tissue anchor during a translumenal procedure. In one embodiment, an apparatus suitable for facilitating removal of a lymph node comprises an expandable device including at least one deployable member having contracted and expanded states. The deployable member may be delivered in the contacted state to a location distal to the lymph node using an insertion tool adapted to be disposed beyond the lymph node. In the expanded state, the deployable member comprises a configuration sized to at least partially circumferentially surround and engage the lymph node. In an alternative embodiment, the deployable member may anchor into an outer portion of a visceral wall to promote stabilization of a system during a medical procedure.

6 Claims, 10 Drawing Sheets

(56) References Cited

U.S. PATENT DOCUMENTS

| | | |
|---|---|---|
| 3,399,432 A | 9/1968 | Merser |
| 3,470,834 A | 10/1969 | Bone |
| 3,556,079 A | 1/1971 | Omizo |
| 3,814,104 A | 6/1974 | Irnich et al. |
| 3,856,016 A | 12/1974 | Davis |
| 3,954,108 A | 5/1976 | Davis |
| 3,958,576 A | 5/1976 | Komiya |
| 4,006,747 A | 2/1977 | Kronenthal et al. |
| 4,204,541 A | 5/1980 | Kapitanov |
| 4,217,902 A | 8/1980 | March |
| 4,235,238 A | 11/1980 | Ogiu et al. |
| 4,485,816 A | 12/1984 | Krumme |
| 4,621,639 A | 11/1986 | Transue et al. |
| 4,749,114 A | 6/1988 | Green |
| 4,773,420 A | 9/1988 | Green |
| 4,791,707 A | 12/1988 | Tucker |
| 4,796,627 A | 1/1989 | Tucker |
| 4,821,939 A | 4/1989 | Green |
| 4,832,027 A | 5/1989 | Utz |
| 4,990,156 A | 2/1991 | Lefebvre |
| 5,015,249 A | 5/1991 | Nakao et al. |
| 5,049,153 A | 9/1991 | Nakao et al. |
| 5,059,205 A | 10/1991 | El-Nounou et al. |
| 5,084,057 A | 1/1992 | Green et al. |
| 5,099,827 A | 3/1992 | Melzer et al. |
| 5,100,420 A | 3/1992 | Green et al. |
| 5,123,914 A | 6/1992 | Cope |
| 5,156,609 A | 10/1992 | Nakao et al. |
| 5,192,303 A | 3/1993 | Gatturna et al. |
| 5,203,787 A | 4/1993 | Noblitt et al. |
| 5,242,456 A | 9/1993 | Nash et al. |
| 5,324,307 A | 6/1994 | Jarrett et al. |
| 5,333,624 A | 8/1994 | Tovey |
| 5,334,217 A | 8/1994 | Das |
| 5,350,385 A | 9/1994 | Christy |
| 5,366,480 A | 11/1994 | Corriveau et al. |
| 5,368,600 A | 11/1994 | Failla et al. |
| 5,368,602 A | 11/1994 | de la Torre |
| 5,411,522 A | 5/1995 | Trott |
| 5,417,691 A | 5/1995 | Hayhurst |
| 5,437,266 A | 8/1995 | McPherson |
| 5,520,700 A | 5/1996 | Beyar et al. |
| 5,527,343 A | 6/1996 | Bonutti |
| 5,554,183 A | 9/1996 | Nazari |
| 5,573,543 A | 11/1996 | Akopov et al. |
| 5,582,615 A | 12/1996 | Foshee et al. |
| 5,582,616 A | 12/1996 | Bolduc et al. |
| 5,593,414 A | 1/1997 | Shipp et al. |
| 5,662,683 A | 9/1997 | Kay |
| 5,667,527 A | 9/1997 | Cook et al. |
| 5,674,231 A | 10/1997 | Green et al. |
| 5,690,656 A | 11/1997 | Cope et al. |
| 5,695,525 A | 12/1997 | Mulhauser et al. |
| 5,728,116 A | 3/1998 | Rosenman |
| 5,741,278 A | 4/1998 | Stevens |
| 5,779,720 A | 7/1998 | Walder-Utz et al. |
| 5,810,848 A | 9/1998 | Hayhurst |
| 5,865,791 A | 2/1999 | Whayne et al. |
| 5,868,763 A | 2/1999 | Spence et al. |
| 5,891,159 A | 4/1999 | Sherman et al. |
| 5,968,078 A | 10/1999 | Grotz |
| 5,972,002 A | 10/1999 | Bark et al. |
| 5,972,022 A | 10/1999 | Huxel |
| 5,976,159 A | 11/1999 | Bolduc et al. |
| 5,984,917 A | 11/1999 | Fleischman et al. |
| 5,984,949 A | 11/1999 | Levin |
| 6,110,183 A | 8/2000 | Cope |
| 6,113,612 A | 9/2000 | Swanson et al. |
| RE36,974 E | 11/2000 | Bonutti |
| 6,149,658 A | 11/2000 | Gardiner et al. |
| 6,152,935 A | 11/2000 | Kammerer et al. |
| 6,152,937 A | 11/2000 | Peterson et al. |
| 6,156,044 A | 12/2000 | Kammerer et al. |
| 6,159,223 A | 12/2000 | Danks et al. |
| 6,171,321 B1 | 1/2001 | Gifford, III et al. |
| 6,183,486 B1 | 2/2001 | Snow et al. |
| 6,193,732 B1 | 2/2001 | Frantzen et al. |
| 6,221,071 B1 * | 4/2001 | Sherry et al. ............ 606/41 |
| 6,228,055 B1 | 5/2001 | Foerster et al. |
| 6,241,747 B1 | 6/2001 | Ruff |
| 6,290,674 B1 | 9/2001 | Roue et al. |
| 6,306,150 B1 | 10/2001 | Levinson |
| 6,328,727 B1 | 12/2001 | Frazier et al. |
| 6,371,963 B1 * | 4/2002 | Nishtala et al. ............ 606/113 |
| 6,402,765 B1 | 6/2002 | Monassevitch et al. |
| 6,419,669 B1 | 7/2002 | Frazier et al. |
| 6,425,887 B1 | 7/2002 | McGuckin et al. |
| 6,425,900 B1 | 7/2002 | Knodel et al. |
| 6,428,548 B1 | 8/2002 | Durgin et al. |
| 6,446,854 B1 | 9/2002 | Remiszewski et al. |
| 6,447,530 B1 | 9/2002 | Ostrovsky et al. |
| 6,468,290 B1 | 10/2002 | Weldon et al. |
| 6,482,178 B1 | 11/2002 | Andrews et al. |
| 6,491,707 B2 | 12/2002 | Makower et al. |
| 6,551,333 B2 | 4/2003 | Kuhns et al. |
| 6,572,629 B2 | 6/2003 | Kalloo et al. |
| 6,592,559 B1 | 7/2003 | Pakter et al. |
| 6,623,510 B2 | 9/2003 | Carley et al. |
| 6,641,557 B1 | 11/2003 | Frazier et al. |
| 6,699,256 B1 | 3/2004 | Logan et al. |
| 6,699,263 B2 | 3/2004 | Cope |
| 6,712,804 B2 | 3/2004 | Roue et al. |
| 6,719,777 B2 | 4/2004 | Ginn et al. |
| 6,746,458 B1 | 6/2004 | Cloud |
| 6,746,460 B2 | 6/2004 | Gannoe et al. |
| 6,746,472 B2 | 6/2004 | Frazier et al. |
| 6,776,783 B1 | 8/2004 | Frantzen et al. |
| 6,849,078 B2 | 2/2005 | Durgin et al. |
| 6,884,248 B2 | 4/2005 | Bolduc et al. |
| 6,911,032 B2 | 6/2005 | Jugenheimer et al. |
| 6,913,607 B2 | 7/2005 | Ainsworth et al. |
| 6,966,916 B2 | 11/2005 | Kumar |
| 6,994,713 B2 | 2/2006 | Berg et al. |
| 7,001,398 B2 | 2/2006 | Carley et al. |
| 7,018,388 B2 | 3/2006 | Yencho et al. |
| 7,025,756 B2 | 4/2006 | Frazier et al. |
| 7,056,325 B1 | 6/2006 | Makower et al. |
| 7,060,084 B1 | 6/2006 | Loshakove et al. |
| 7,087,073 B2 | 8/2006 | Bonutti |
| 7,112,214 B2 | 9/2006 | Peterson et al. |
| 7,115,110 B2 | 10/2006 | Frazier et al. |
| 7,211,101 B2 | 5/2007 | Carley et |
| 7,326,221 B2 | 2/2008 | Sakamoto |
| 7,326,231 B2 | 2/2008 | Phillips et al. |
| 7,331,968 B2 | 2/2008 | Arp et al. |
| 7,410,460 B2 | 8/2008 | Benderev |
| 7,416,554 B2 | 8/2008 | Lam et al. |
| 7,485,124 B2 | 2/2009 | Kuhns et al. |
| 7,494,496 B2 | 2/2009 | Swain et al. |
| 7,601,159 B2 | 10/2009 | Ewers et al. |
| 7,608,091 B2 | 10/2009 | Goldbarb et al. |
| 7,618,426 B2 | 11/2009 | Ewers et al. |
| 7,621,925 B2 | 11/2009 | Saadat et al. |
| 7,622,068 B2 | 11/2009 | Li et al. |
| 7,641,836 B2 | 1/2010 | Li et al. |
| 7,655,015 B2 | 2/2010 | Goldfarb et al. |
| 7,666,197 B2 | 2/2010 | Orban, III |
| 7,670,362 B2 | 3/2010 | Zergiebel |
| 7,695,493 B2 | 4/2010 | Saadat et al. |
| 7,704,264 B2 | 4/2010 | Ewers et al. |
| 7,722,628 B2 | 5/2010 | Stokes et al. |
| 7,727,247 B2 | 6/2010 | Kimura et al. |
| 7,727,248 B2 | 6/2010 | Smith et al. |
| 7,736,376 B2 | 6/2010 | Sato et al. |
| 7,736,378 B2 | 6/2010 | Maahs et al. |
| 7,736,379 B2 | 6/2010 | Ewers et al. |
| 7,736,388 B2 | 6/2010 | Goldfarb et al. |
| 7,744,613 B2 | 6/2010 | Ewers et al. |
| 7,758,598 B2 | 7/2010 | Conlon et al. |
| 7,758,612 B2 | 7/2010 | Shipp |
| 7,799,040 B2 | 9/2010 | Stokes et al. |
| 7,803,165 B2 | 9/2010 | Stokes et al. |
| 7,803,166 B2 | 9/2010 | Stokes et al. |
| 7,815,652 B2 | 10/2010 | Messerly et al. |

(56) References Cited

U.S. PATENT DOCUMENTS

| | | |
|---|---|---|
| 7,815,653 B2 | 10/2010 | Stokes et al. |
| 7,815,659 B2 | 10/2010 | Conlon et al. |
| 7,815,662 B2 | 10/2010 | Spivey et al. |
| 7,828,811 B2 | 11/2010 | Kortenbach et al. |
| 2001/0002250 A1* | 5/2001 | Burbank et al. ............... 424/9.5 |
| 2001/0037130 A1 | 11/2001 | Adams |
| 2001/0039435 A1 | 11/2001 | Roue et al. |
| 2003/0158578 A1 | 8/2003 | Pantages et al. |
| 2003/0195561 A1 | 10/2003 | Carley et al. |
| 2004/0009289 A1 | 1/2004 | Carley et al. |
| 2004/0039414 A1 | 2/2004 | Carley et al. |
| 2004/0044364 A1 | 3/2004 | Devries et al. |
| 2004/0073236 A1 | 4/2004 | Carley et al. |
| 2004/0087981 A1 | 5/2004 | Berube et al. |
| 2004/0087985 A1 | 5/2004 | Loshakove et al. |
| 2004/0092975 A1 | 5/2004 | Loshakove et al. |
| 2004/0097982 A1 | 5/2004 | Jugenheimer et al. |
| 2004/0167539 A1 | 8/2004 | Kuehn et al. |
| 2004/0186514 A1 | 9/2004 | Swain et al. |
| 2004/0220596 A1 | 11/2004 | Frazier et al. |
| 2005/0015141 A1 | 1/2005 | Quiachon et al. |
| 2005/0033313 A1* | 2/2005 | Chu et al. ...................... 606/114 |
| 2005/0038370 A1 | 2/2005 | Kuth et al. |
| 2005/0113851 A1 | 5/2005 | Swain et al. |
| 2005/0119695 A1 | 6/2005 | Carley et al. |
| 2005/0143763 A1 | 6/2005 | Ortiz et al. |
| 2005/0171562 A1 | 8/2005 | Criscuolo et al. |
| 2005/0182445 A1 | 8/2005 | Zamierowski |
| 2005/0192596 A1 | 9/2005 | Jugenheimer et al. |
| 2005/0197594 A1 | 9/2005 | Burbank et al. |
| 2005/0234512 A1 | 10/2005 | Nakao |
| 2005/0251165 A1 | 11/2005 | Vaughan et al. |
| 2005/0277945 A1 | 12/2005 | Saadat et al. |
| 2005/0277981 A1 | 12/2005 | Maahs et al. |
| 2005/0283188 A1 | 12/2005 | Loshakove et al. |
| 2006/0004409 A1 | 1/2006 | Nobis et al. |
| 2006/0004410 A1 | 1/2006 | Nobis et al. |
| 2006/0015006 A1 | 1/2006 | Laurence et al. |
| 2006/0015125 A1 | 1/2006 | Swain |
| 2006/0025788 A1 | 2/2006 | Loshakove et al. |
| 2006/0025819 A1 | 2/2006 | Nobis et al. |
| 2006/0106279 A1 | 5/2006 | Machold et al. |
| 2006/0106405 A1 | 5/2006 | Fann et al. |
| 2006/0116605 A1 | 6/2006 | Nakao |
| 2006/0135989 A1 | 6/2006 | Carley et al. |
| 2006/0155288 A1 | 7/2006 | Little et al. |
| 2006/0167484 A1 | 7/2006 | Carley et al. |
| 2006/0190016 A1 | 8/2006 | Onuki et al. |
| 2006/0190038 A1 | 8/2006 | Carley et al. |
| 2006/0206063 A1 | 9/2006 | Kagan et al. |
| 2006/0207606 A1 | 9/2006 | Roue et al. |
| 2006/0217762 A1 | 9/2006 | Maahs et al. |
| 2006/0235447 A1 | 10/2006 | Walshe |
| 2006/0237022 A1 | 10/2006 | Chen et al. |
| 2006/0237023 A1 | 10/2006 | Cox et al. |
| 2006/0241662 A1 | 10/2006 | Adams et al. |
| 2006/0241691 A1 | 10/2006 | Wilk |
| 2006/0253144 A1 | 11/2006 | Mikkaichi |
| 2006/0271073 A1 | 11/2006 | Lam et al. |
| 2006/0271101 A1 | 11/2006 | Saadat et al. |
| 2007/0010835 A1 | 1/2007 | Breton et al. |
| 2007/0100375 A1 | 5/2007 | Mikkaichi et al. |
| 2007/0100376 A1 | 5/2007 | Mikkaichi et al. |
| 2007/0112362 A1 | 5/2007 | Mikkaichi et al. |
| 2007/0123840 A1 | 5/2007 | Cox |
| 2007/0129755 A1 | 6/2007 | Abbott et al. |
| 2007/0173868 A1 | 7/2007 | Bachinski et al. |
| 2007/0208360 A1 | 9/2007 | Demarais et al. |
| 2007/0219411 A1 | 9/2007 | Dejima et al. |
| 2007/0270752 A1 | 11/2007 | LaBombard |
| 2007/0270943 A1 | 11/2007 | Solem et al. |
| 2007/0276416 A1 | 11/2007 | Ginn et al. |
| 2007/0276424 A1 | 11/2007 | Mikkaichi et al. |
| 2008/0015633 A1 | 1/2008 | Abbott et al. |
| 2008/0086153 A1 | 4/2008 | Sakamoto et al. |
| 2008/0091059 A1 | 4/2008 | Machold |
| 2008/0097489 A1 | 4/2008 | Goldfarb et al. |
| 2008/0114378 A1 | 5/2008 | Matsushita |
| 2008/0114398 A1 | 5/2008 | Phillips et al. |
| 2008/0147116 A1 | 6/2008 | Smith et al. |
| 2008/0154290 A1 | 6/2008 | Golden et al. |
| 2008/0172088 A1 | 7/2008 | Smith et al. |
| 2008/0177304 A1 | 7/2008 | Westra et al. |
| 2008/0200930 A1 | 8/2008 | Saadat et al. |
| 2008/0208161 A1 | 8/2008 | Kaji et al. |
| 2008/0208214 A1 | 8/2008 | Sato et al. |
| 2008/0208218 A1 | 8/2008 | Shiono |
| 2008/0208219 A1 | 8/2008 | Suzuki |
| 2008/0208220 A1 | 8/2008 | Shiono et al. |
| 2008/0208251 A1 | 8/2008 | Weadock et al. |
| 2008/0221619 A1 | 9/2008 | Spivey et al. |
| 2008/0228199 A1 | 9/2008 | Cropper et al. |
| 2008/0228202 A1 | 9/2008 | Cropper et al. |
| 2008/0228203 A1 | 9/2008 | Bell et al. |
| 2008/0243148 A1 | 10/2008 | Mikkaichi et al. |
| 2008/0255422 A1 | 10/2008 | Kondoh et al. |
| 2008/0255423 A1 | 10/2008 | Kondo et al. |
| 2008/0262525 A1 | 10/2008 | Chang et al. |
| 2008/0269566 A1 | 10/2008 | Measamer |
| 2008/0275297 A1 | 11/2008 | Bakos et al. |
| 2008/0281354 A1 | 11/2008 | Cropper et al. |
| 2008/0294178 A1 | 11/2008 | Kortenbach et al. |
| 2008/0296344 A1 | 12/2008 | Cropper et al. |
| 2008/0300547 A1 | 12/2008 | Bakos |
| 2008/0300608 A1 | 12/2008 | Measamer |
| 2008/0300624 A1 | 12/2008 | Schwemberger et al. |
| 2008/0300627 A1 | 12/2008 | Measamer et al. |
| 2008/0319257 A1 | 12/2008 | Sato et al. |
| 2009/0005800 A1 | 1/2009 | Franer et al. |
| 2009/0018552 A1 | 1/2009 | Lam et al. |
| 2009/0069822 A1 | 3/2009 | Takahashi et al. |
| 2009/0088780 A1 | 4/2009 | Shiono et al. |
| 2009/0088797 A1 | 4/2009 | Crombie et al. |
| 2009/0125038 A1 | 5/2009 | Ewers et al. |
| 2009/0125039 A1 | 5/2009 | Mikkaichi et al. |
| 2009/0204147 A1* | 8/2009 | Rahmani ...................... 606/232 |
| 2009/0222029 A1 | 9/2009 | Gordin et al. |
| 2009/0287080 A1 | 11/2009 | Nishina et al. |
| 2009/0299385 A1 | 12/2009 | Stefanchik et al. |
| 2009/0299406 A1 | 12/2009 | Swain et al. |
| 2009/0306686 A1 | 12/2009 | Ohdaira |
| 2009/0318936 A1 | 12/2009 | Harris et al. |
| 2009/0326578 A1 | 12/2009 | Ewers et al. |
| 2010/0010457 A1 | 1/2010 | Ewers et al. |
| 2010/0010508 A1 | 1/2010 | Takahashi et al. |
| 2010/0010509 A1 | 1/2010 | Ishioka et al. |
| 2010/0010511 A1 | 1/2010 | Harris et al. |
| 2010/0010514 A1 | 1/2010 | Ishioka et al. |
| 2010/0010520 A1 | 1/2010 | Takahashi et al. |
| 2010/0042115 A1 | 2/2010 | Saadat et al. |
| 2010/0042144 A1 | 2/2010 | Bennett |
| 2010/0049244 A1 | 2/2010 | Cohen et al. |
| 2010/0076462 A1 | 3/2010 | Bakos et al. |
| 2010/0076488 A1 | 3/2010 | Spivey et al. |
| 2010/0094341 A1 | 4/2010 | Raju |
| 2010/0106166 A1 | 4/2010 | Cropper et al. |
| 2010/0113873 A1 | 5/2010 | Suzuki et al. |
| 2010/0121351 A1 | 5/2010 | Whitfield et al. |
| 2010/0174312 A1 | 7/2010 | Maahs et al. |
| 2010/0198192 A1 | 8/2010 | Serina et al. |
| 2010/0211086 A1 | 8/2010 | Ewers et al. |
| 2010/0217292 A1 | 8/2010 | Kimura et al. |
| 2010/0217293 A1 | 8/2010 | Kimura et al. |
| 2010/0217294 A1 | 8/2010 | Kimura et al. |
| 2010/0249498 A1 | 9/2010 | Wingardner et al. |
| 2010/0256658 A1 | 10/2010 | Criscuolo et al. |
| 2010/0264192 A1 | 10/2010 | Marczyk |
| 2010/0268253 A1 | 10/2010 | Ahlberg et al. |

(56) References Cited

U.S. PATENT DOCUMENTS

2010/0268270 A1 10/2010 Viola
2011/0022065 A1 1/2011 Shipp

FOREIGN PATENT DOCUMENTS

| | | |
|---|---|---|
| EP | 1317904 A1 | 11/2003 |
| EP | 1961388 A2 | 8/2008 |
| JP | 2002-523126 | 7/2002 |
| JP | 2008-510596 | 4/2008 |
| WO | WO88/01486 | 3/1988 |
| WO | WO90/02522 | 3/1990 |
| WO | WO95/21575 | 8/1995 |
| WO | WO96/14020 | 5/1996 |
| WO | WO96/40356 | 12/1996 |
| WO | WO98/18389 | 5/1998 |
| WO | WO99/62408 | 12/1999 |
| WO | WO00/07506 | 2/2000 |
| WO | WO00/10471 | 3/2000 |
| WO | WO00/16701 | 3/2000 |
| WO | WO00/21443 | 4/2000 |
| WO | WO00/56223 | 9/2000 |
| WO | WO00/56227 | 9/2000 |
| WO | WO01/19256 | 3/2001 |
| WO | WO01/35832 | 5/2001 |
| WO | WO01/58363 | 8/2001 |
| WO | WO2005/034729 | 4/2005 |
| WO | WO2007/004228 | 1/2007 |
| WO | WO2007/035177 | 3/2007 |
| WO | WO2007/089843 | 8/2007 |
| WO | WO2007/142977 | 12/2007 |
| WO | WO2007/024615 | 3/2009 |

OTHER PUBLICATIONS

Office Action for Australian Patent Application 2009282596 dated Feb. 14, 2013, 3 pgs.
Office Action for Canadian Patent Application 2733933 dated Sep. 4, 2012, 2 pgs.
Response to Office Action for Canadian Patent Application 2733933 dated Feb. 28, 2013, 19 pgs.
Notice of Allowance for Canadian Patent Application 2733933 dated Jun. 27, 2013, 1 pg.
Communication Pursuant to Rules 161(1) and 162EPC for European Patent Application Serial No. 09791618.3, dated Mar. 28, 2011, 2 pages.
Response to Communication Pursuant to Rules 161(1) and 162EPC for European Patent Application Serial No. 09791618.3, dated May 6, 2011, 4 pages.
International Search Report for PCT/US2009/041415, dated Jul. 24, 2009, 4 pages.
International Preliminary Report on Patentability for PCT/US2009/041415, dated Nov. 4, 2010, 6 pages.
International Search Report for PCT/US2009/054176, dated Nov. 20, 2009, 16 pages.
International Preliminary Report on Patentability for PCT/US2009/054176, dated Mar. 3, 2011, 9 pages.
International Search Report for PCT/US2009/056512, dated Feb. 10, 2010, 5 pages.
Article 34 Demand and Amendment for PCT/US2009/056512, dated Jul. 6, 2010, 22 pages.
International Preliminary Report on Patentability for PCT/US2009/056512, dated Jan. 10, 2010, 31 pages.
International Search Report and Written Opinion for PCT/US2009/056604, dated May 4, 2010, 9 pages.
International Search Report for PCT/US2009/066983, dated Jan. 19, 2010, 4 pages.
International Search Report and Written Opinion for PCT/US2009/066992, dated Mar. 4, 2010, 15 pages.
International Search Report and Written Opinion for PCT/US2009/067992, Jul. 9, 2010, 20 pages.
International Search Report and Written Opinion for PCT/US2009/067994, dated Jun. 10, 2010, 18 pages.
International Search Report and Written Opinion for PCT/US2010/036188, dated Sep. 14, 2010, 18 pages.
Restriction Requirement for U.S. Appl. No. 12/428,226, dated Apr. 27, 2011, 7 pages.
Response to Restriction Requirement for U.S. Appl. No. 12/428,226, dated May 27, 2011, 10 pages.
Office Action for U.S. Appl. No. 12/428,226, dated Jun. 9, 2011, 8 pages.
Office Action for U.S. Appl. No. 12/543,000, dated Mar. 15, 2011, 14 pages.
Fritscher-Ravens, "Transgastric endoscopy—a new fashion, a new excitement!", *Endoscopy*, vol. 39, 2007, pp. 161-167.
Sporn et al., "Endoscopic colotomy closure after full thickness excision: comparison of T fastener with mutliclip applier", *Endoscopy*, vol. 40, 2008, pp. 589-594.
Voermans et al., "In vitro comparison and evaluation of seven gastric closure modalities for natural orifice transluminal endoscopic surgery", *Endoscopy*, vol. 40, 2008, pp. 595-601.
Sclabas et al., "Endoluminal Methods for Gastrotomy Closure in Natural Orifice TransEnteric Surgery", *Surgical Innovation*, vol. 13, No. 1, Mar. 2006, pp. 23-30.
Desilets et al., "Loop-anchor purse-string versus endoscopic clips for gastric closure: a natural orifice transluminal endoscopic surgery comparison study using burst pressures", *Gastrointestinal Endoscopy*, vol. 70, No. 6, 2009, pp. 1225-1230.
Sporn et al., "Endoscopic colotomy closure for natural orifice transluminal endoscopic surgery using a T-fastener protoype in comparison to conventional laparoscopic suture closure", *Gastrointestinal Endoscopy*, vol. 68, No. 4, 2008, pp. 724-730.
Dray et al., "Air and fluid leak tests after Notes procedures: a pilot study in a live porcine model", *Gastrointestinal Endoscopy*, vol. 68, No. 3, 2008, pp. 513-519.
Shurr et al., "An over-the-scope clip (OTSC) system for closure of iatrogenic colon perforations: results of an experimental survival study in pigs", *Endoscopy*, vol. 40, 2008, pp. 584-588.
Romanelli et al, "Natural orifice transluminal endoscopic surgery gastrotomy closure in porcine explants with the Padlock-G clip using the Lock-It system", *Endoscopy*, vol. 42, 2010, pp. 306-310.
Bergström et al., "Early clinical experience with a new flexible endoscopic suturing method for natural orifice transluminal endoscopic surgery and intraluminal endosurgery", *Gastrointestinal Endoscopy*, vol. 67, No. 3, 2008, pp. 528-533.
Park et al, "Endoscopic sutured closure of a gastric natural orifice transluminal endoscopic surgery access gastronomy compared with open surgical closure in a porcine model. A randomized, multicenter controlled trial", *Endoscopy*, vol. 42, 2010 pp. 311-317.
Yasser M. Bhat, MD, "Transluminal Endosurgery: Novel Use of Endoscopic Tacks for the Closure of Access Sites in Natural Orifice Transluminal Endoscopic Surgery," *Gastrointestinal Endoscopy*, vol. 69, No. 6, p. 1161, 2009.

\* cited by examiner

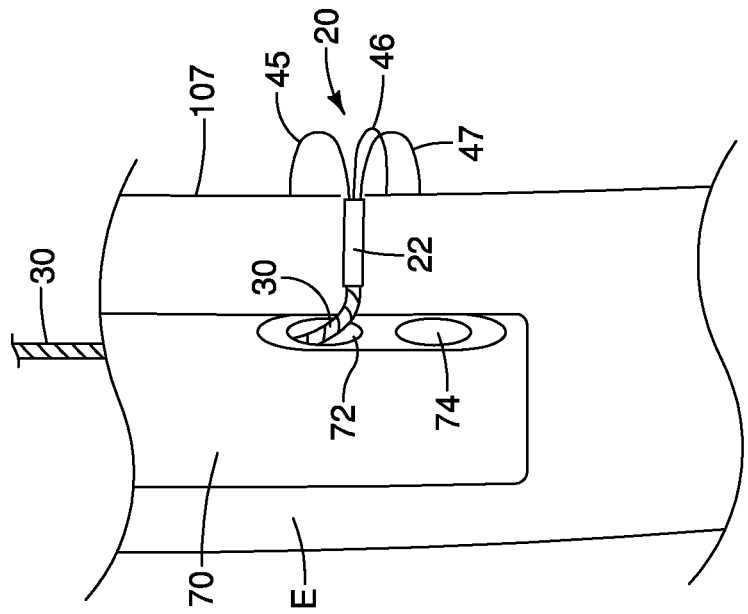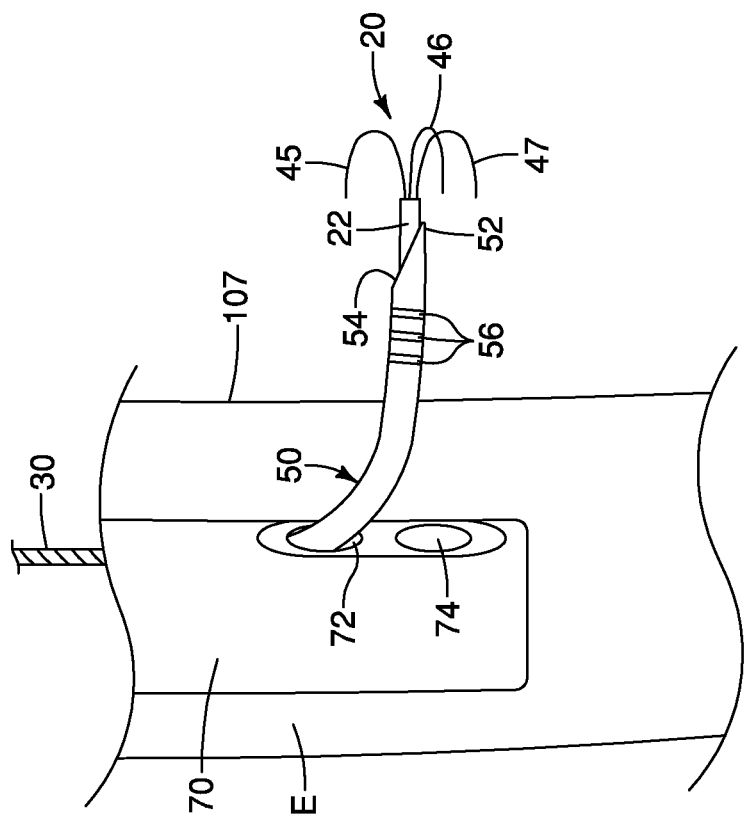

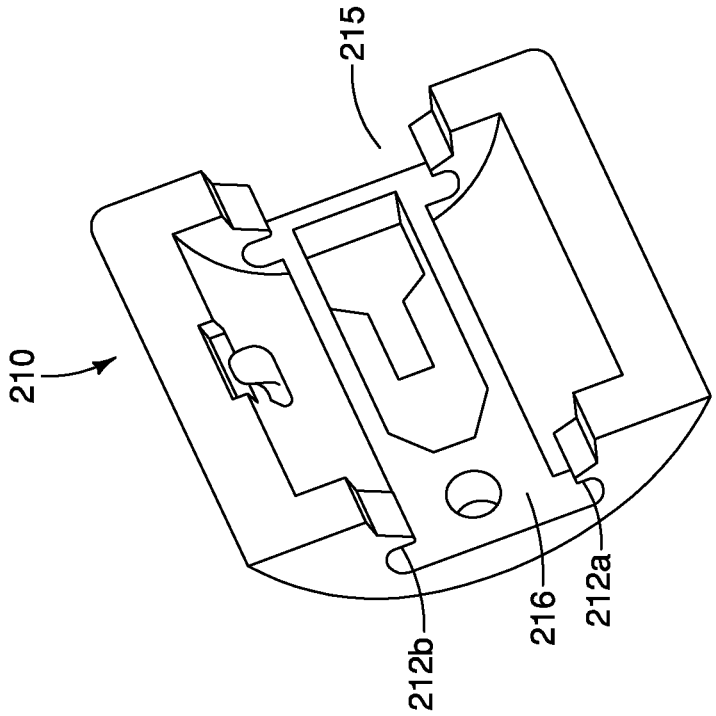
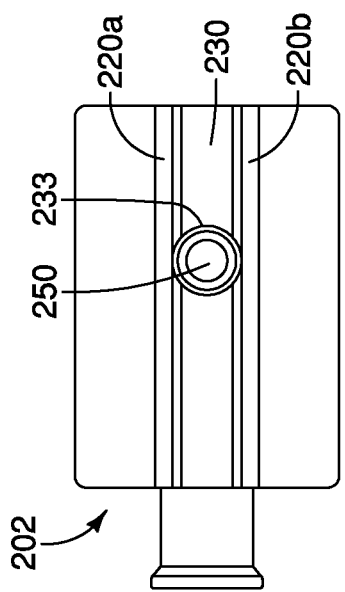
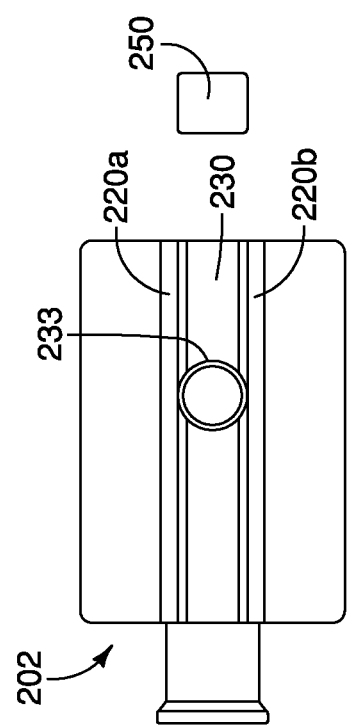

APPARATUS AND METHODS FOR REMOVING LYMPH NODES OR ANCHORING INTO TISSUE DURING A TRANSLUMENAL PROCEDURE

PRIORITY CLAIM

This invention claims the benefit of priority of U.S. Provisional Application Ser. No. 61/090,115, entitled "Apparatus and Methods for Removing Lymph Nodes or Anchoring into Tissue During a Translumenal Procedure," filed Aug. 19, 2008, the disclosure of which is hereby incorporated by reference in its entirety.

BACKGROUND

The present embodiments relate generally to medical devices, and more particularly, apparatus and methods suitable for removing lymph nodes or providing a tissue anchor during a translumenal medical procedure.

Translumenal procedures generally encompass the formation of perforations in visceral walls to gain access to adjacent structures of the body. For example, culdoscopy was developed over 70 years ago, and involves transvaginally accessing the peritoneal cavity by forming a perforation in the cul de sac. This access to the peritoneal cavity allows medical professionals to visually inspect numerous anatomical structures, as well as perform various procedures such as biopsies or other operations. Many translumenal procedures for gaining access to different body cavities using other bodily lumens have also been developed. Generally, each of the translumenal procedures require the use of several different medical instruments, such as a cutting instrument to form the perforation, an endoscope or other visualizing device to inspect the area or otherwise perform some procedure, and then a closure instrument to close the perforation.

Relatively recent attempts have focused on the translumenal removal of lymph nodes. See Fritscher-Ravens, et al., "*Endoscopic Transgastric Lymphadenectomy Using Endoscopic Ultrasound For Selection and Guidance,*" *Gastrointestinal Endoscopy*, Vol. 63, Issue 2, pp. 302-306 (2006). In this article, selected lymph nodes were punctured with a 19-gauge Endoscopic Ultrasound (EUS) needle. A metal anchor with thread, loaded onto the needle, was placed across the lymph node to pull the node toward the stomach. After gastric-wall dissection with a needle knife at the point of emergence of the thread, the nodes were removed by pulling on the thread and the anchor. The gastric incision then was closed with an endoscopic suturing system.

While the above-referenced article provides a foundation for translumenal removal of lymph nodes, it is an emerging approach and merits the development of new and improved techniques.

SUMMARY

In a first embodiment according to the teachings of the present invention, apparatus and methods are provided for facilitating removal of one or more lymph nodes. The apparatus preferably comprises an expandable device including at least one deployable member having contracted and expanded states. In the expanded state, the deployable member may comprise a parachute-shaped configuration, umbrella-shaped configuration, or other configuration sized to at least partially circumferentially surround the lymph node. The deployable member may be delivered to a location distal to the lymph node using an insertion tool adapted to be disposed beyond the lymph node.

In one exemplary method of use, the insertion tool may be advanced beyond the lymph node, and a T-anchor coupled to a suture may be advanced through the insertion tool and ejected at a location distal to the lymph node. Retraction of the suture causes the T-anchor to engage the lymph node and promotes stabilization of the lymph node. Subsequently, the deployable member is advanced distal to the lymph node in the contracted state, using the same insertion device or another insertion device, and assumes the expanded state when advanced distal to the insertion tool and the lymph node.

The lymph node may be removed translumenally through a visceral wall, such as the stomach or esophagus. In one method step, an opening may be created in the visceral wall to facilitate removal of the lymph node. The deployable member may be proximally retracted to engage and retract the lymph node in a proximal direction through the opening in the visceral wall to facilitate removal of the lymph node. A removal device, such as a snare, may then be used to disengage the lymph node from surrounding tissue.

The deployable member may comprise a nickel-titanium alloy that is configured to self-expand to the parachute-shaped configuration or another suitable configuration. The parachute-shaped configuration may be suitable for at least partially circumferentially surrounding the lymph node, and may comprise a strength sufficient to engage and retract the lymph node. In one embodiment, three parachute-shaped deployable members are provided, although greater or fewer deployable members may be used.

In an alternative embodiment, the expandable device may be anchored into tissue to promote stability of a system during a medical procedure. In this method, an insertion tool may be advanced through a first channel of an endoscope, and may pierce through an outer portion of the visceral wall. The expandable device is advanced through the insertion tool and the deployable member is deployed distal to the insertion tool. Upon proximal retraction, the deployable member anchors into the outer portion of the visceral wall. Such anchoring promotes stabilization of the system when additional components are advanced, or procedures performed, through the first channel or a second channel of the endoscope.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIGS. 13-14 are exemplary method steps illustrating use of the expandable device of FIGS. 1-2B as a visceral wall anchor.

FIGS. 18A-18B are side schematic views of the control assembly of FIGS. 17A-17B with a slidable actuator removed for illustrative purposes.

FIG. 19 is a rear perspective view of a slidable actuator of the control assembly of FIGS. 17A-17B.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Figure 1:
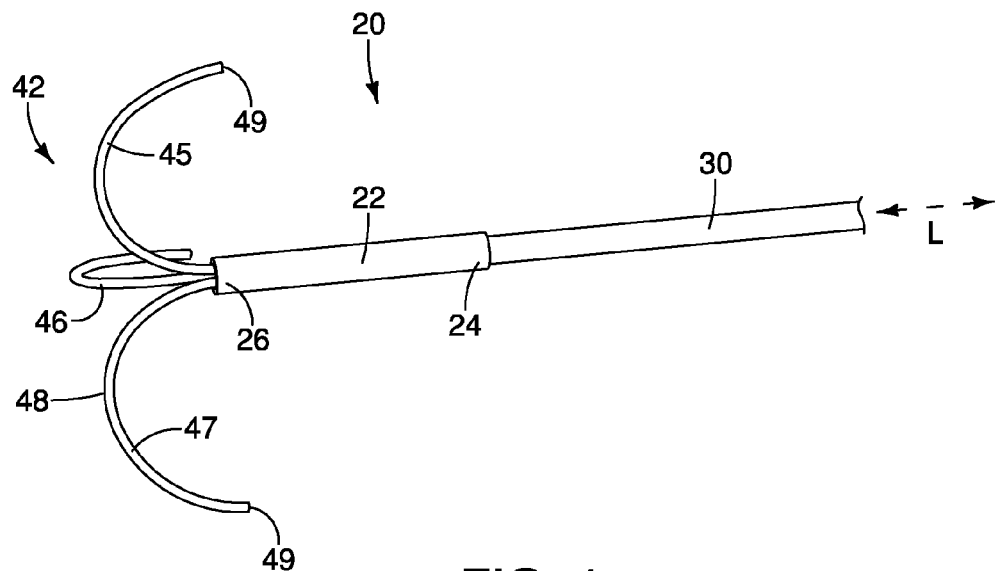
FIG. 1 is a perspective view of a distal end of an expandable device.

Referring now to FIG. 1, a first embodiment of an expandable device 20 is shown. In this embodiment, the expandable device 20 comprises at least one tube member 22 having a proximal end 24 and a distal end 26. The expandable device 20 further comprises a distal deployment mechanism 42. In the embodiment of FIG. 1, the distal deployment mechanism 42 comprises three deployable members 45-47. The deployable members 45-47 extend distally from the distal end 26 of the tube member 22, as shown in FIG. 1. Further, a control member 30 may extend proximally from the proximal end 24 of the tube member 22.

The deployable members 45-47 each may be affixed relative to the tube member 22. In one embodiment, each of the deployable members 45-47 may be separate and discrete elements. Accordingly, three separate deployable members may be provided. Specifically, the three deployable members 45-47 may be coupled to the distal end 26 of the tube member 22 using an adhesive, frictional fit, mechanical device or other suitable mechanism.

While three deployable members 45-47 are depicted, it will be apparent that greater or fewer deployable members may be employed. Moreover, the deployable members 45-47 may comprise any shape suitable for engaging, penetrating and/or abutting tissue, or for engaging and capturing a lymph node, for purposes explained further below, and need not necessarily assume the expanded shape depicted in FIGS. 1-2A.

The tube member 22 may comprise any suitable shape and material. Solely by way of example, the tube member 22 may comprise stainless steel or a biocompatible plastic. The tube member 22 may be cylindrically-shaped, as depicted in FIG. 1, which may facilitate insertion through a lumen of an insertion tool 50.

Figure 2A:
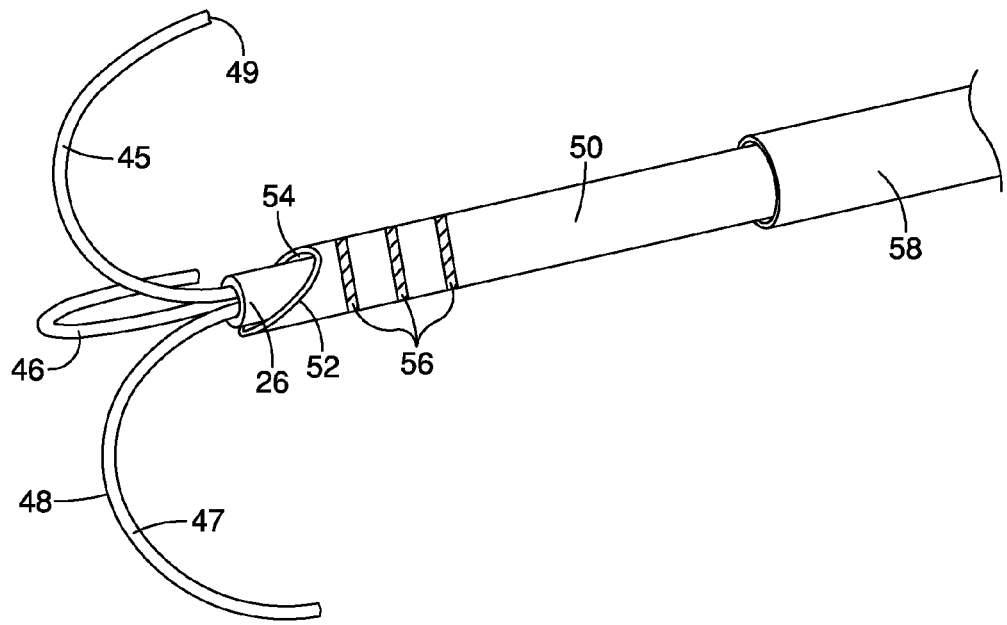
FIG. 2A is a perspective view of a distal region of an insertion tool and the expandable device of FIG. 1.
Figure 2B:
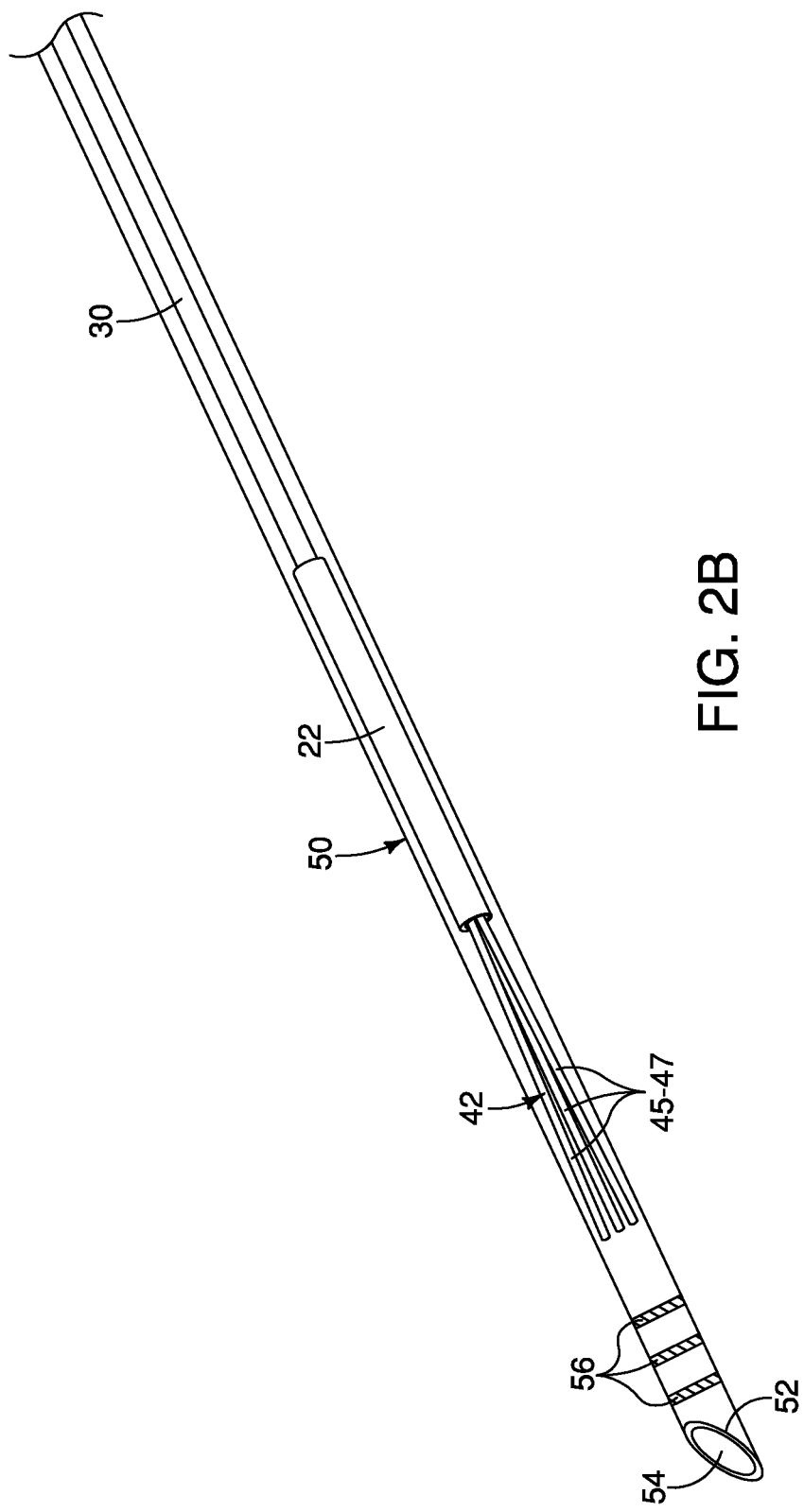
FIG. 2B is a perspective, cut-away view illustrating the expandable device of FIG. 1 in a delivery configuration.

Alternatively, the tube member 22 may be omitted entirely in the case where proximal regions of the deployable members 45-47 are collected together, and preferably affixed together, for example, using a solder or weld. In the latter example, the deployable members 45-47 may be affixed together and soldered or welded directly to a distal portion of the control member 30, or the deployable members 45-47 may be integrally formed as a distal extension of the control member 30. Further, a plurality of wire members may be braided or twisted together along a main portion of their length, but comprise distal regions configured to deploy to the parachute or umbrella-shaped configurations shown herein, or another configuration suitable for engaging the lymph node The deployable members 45-47 each comprise a contracted delivery configuration, as shown in FIG. 2B, and further comprise an expanded deployed configuration, as shown in FIGS. 1-2A. In one embodiment, each of the deployable members 45-47 may comprise a parachute or umbrella-shaped configuration in the expanded state, or another configuration suitable for engaging the lymph node, such as a bent or L-shaped configuration.

Figure 15:
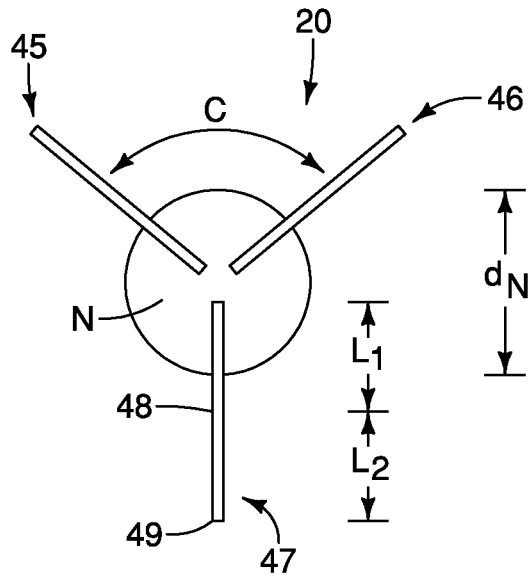
FIG. 15 is an end view of a lymph node and the expandable device of FIGS. 1-2B in a deployed state.

For example, in the parachute or umbrella-shaped configurations shown, the deployable members 45-47 may comprise a curvature of about 90 to about 360 degrees in the expanded state, and more preferably about 180 degrees, as shown in FIGS. 1-2A. Where the deployable members 45-47 "retroflex" and comprises a curvature of about 180 degrees, an apex 48 is formed and the end regions 49 of the deployable members are oriented substantially parallel to the tube member 22. Moreover, the end regions 49 may be radially spaced apart from one another in the expanded state, as best seen in FIG. 1 and FIG. 15 below. In this configuration, the end regions 49 may be well-suited for engaging and capturing lymph nodes, or engaging, grasping and/or abutting tissue, as explained further below.

The dimensions of the expandable device 20 may be tailored based on a particular surgical procedure, a particular patient's anatomy and/or other factors. However, for illustrative purposes, in a lymph node removal procedure, a diameter $d_N$ of an exemplary lymph node N may range from about 5 to about 15 mm, as depicted in FIG. 15. In this example, the longitudinal length of the tube member 22 may range from about 2 mm to about 10 mm, the straightened (delivery or non-curved) length of the deployable members 45-47 may range from about 10 mm to about 50 mm, the outer diameter of the tube member 22 may range from about 0.3 mm to about 1.5 mm, and the outer diameter of the deployable members 45-47 may range from about 0.1 mm to about 0.5 mm.

Further, as shown in FIG. 15 below, a longitudinal length $L_1$ between a longitudinal axis L (see FIG. 1) and the apex 48 may be about 3.2 to 16.0 mm, while a longitudinal length $L_2$ between the longitudinal axis L and the distal tip 49 may be about 6.4 to 32.0 mm. Such dimensions are provided for reference purposes only and are not intended to be limiting. Therefore, if the diameter $d_N$ of an exemplary lymph node N ranges from about 5 to about 15 mm, the expandable device 20 will be configured to substantially or entirely surround, engage, and facilitate removal of the lymph node N, as depicted in FIG. 15 below.

Referring still to FIG. 15, the three deployable members 45-47 may be spaced apart a circumferential distance C, which may be about 120 degrees. As will be apparent, the deployable members 45-47 may be spaced closer together or further apart to facilitate engagement and capture of a lymph node. If additional deployable members are provided, then the circumferential distance C between deployable members may decrease accordingly.

The deployable members 45-47 may comprise a shape-memory material, such as a nickel-titanium alloy (nitinol). If a shape-memory material such as nitinol is employed, the deployable members 45-47 may be manufactured such that they can assume the preconfigured expanded state shown in FIGS. 1-2A upon application of a certain cold or hot medium. More specifically, a shape-memory material may undergo a substantially reversible phase transformation that allows it to "remember" and return to a previous shape or configuration. For example, in the case of nitinol, a transformation between an austenitic phase and a martensitic phase may occur by cooling and/or heating (shape memory effect) or by isothermally applying and/or removing stress (superelastic effect). Austenite is characteristically the stronger phase and martensite is the more easily deformable phase.

In an example of the shape-memory effect, a nickel-titanium alloy having an initial configuration in the austenitic phase may be cooled below a transformation temperature ($M_f$) to the martensitic phase and then deformed to a second configuration. Upon heating to another transformation temperature ($A_f$), the material may spontaneously return to its initial, predetermined configuration, as shown in FIG. 1. Generally, the memory effect is one-way, which means that the spontaneous change from one configuration to another occurs only upon heating. However, it is possible to obtain a two-way shape memory effect, in which a shape memory material spontaneously changes shape upon cooling as well as upon heating.

Alternatively, the deployable members 45-47 may be made from other metals and alloys that are biased, such that they may be restrained by the insertion tool 50 prior to deployment, but are inclined to return to their relaxed, expanded configuration upon deployment. Solely by way of example, the deployable members 45-47 may comprise other materials such as stainless steel, cobalt-chrome alloys, amorphous metals, tantalum, platinum, gold and titanium. The deployable members 45-47 also may be made from non-metallic materials, such as thermoplastics and other polymers. As noted above, the deployable members 45-47 may comprise any shape suitable for engaging and capturing lymph nodes, or engaging, grasping and/or abutting tissue, for purposes explained further below, and need not necessarily assume the curved shape depicted in FIGS. 1-2A.

Figure 9:
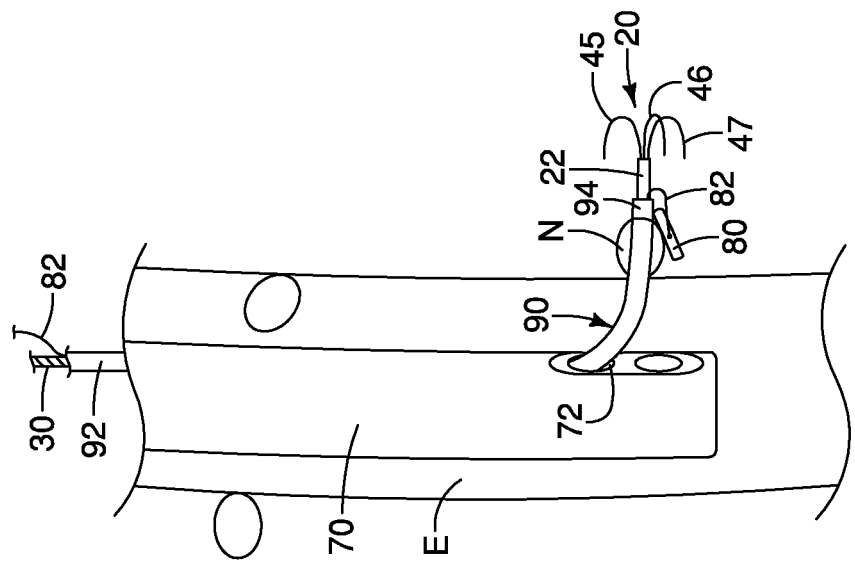
Figure 8:
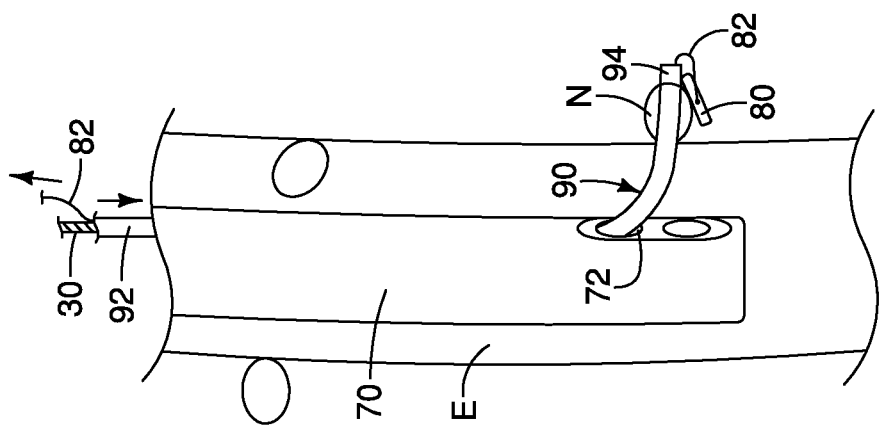

Referring to FIG. 2B, the expandable devices 20 may be delivered to a target site in a patient's anatomy in the contracted configuration using an insertion tool 50. In one embodiment, the insertion tool 50 comprises a needle-like body having a sharpened distal tip 52 and a hollow lumen 54, as shown in FIGS. 2A-2B. The insertion tool 50 may be manufactured from stainless steel or any other suitable material, and may comprise an endoscopic ultrasound (EUS), or echogenic, needle. Solely by way of example, the insertion tool 50 may comprise the EchoTip® Ultrasound Needle, or the EchoTip® Ultra Endoscopic Ultrasound Needle, both manufactured by Cook Endoscopy of Winston-Salem, N.C. Alternatively, the insertion tool 50 may comprise a non-echogenic needle, which may be visualized using an endoscope. As a further alternative, the insertion tool may comprise a conventional catheter 90 having at least one lumen sized to receive the expandable device 20, as depicted in FIGS. 8-9 below.

The hollow lumen 54 of the insertion tool 50 may comprise an inner diameter than is larger than an outer diameter of the expandable device 20. Therefore, the expandable device 20 may be loaded into the hollow lumen 54 in a delivery configuration, as shown in FIG. 2B. In the delivery configuration, the deployable members 45-47 of the expandable device 20 may comprise a substantially longitudinally-oriented profile, i.e., oriented along a longitudinal axis of the insertion tool 50. The expandable device 20 may be ejected from the insertion tool 50 by distally advancing a proximal region of the control member 30 while holding the insertion tool 50 steady, as explained in further detail below.

The insertion tool 50 may comprise one or more markers 56, as shown in FIGS. 2A-2B, which may be disposed near the distal end of the insertion tool 50. The markers 56 may be configured to be visualized under fluoroscopy of other imaging techniques to facilitate location of the distal end of the insertion tool, for example, so that a physician may determine how far the insertion tool 50 has penetrated through a visceral wall, lymph node, or other matter, as explained further below. Optionally, a sheath member 58 having an inner diameter larger than an outer diameter of the insertion tool 50, as shown in FIG. 2A, may be longitudinally advanced over the insertion tool 50 to prevent inadvertent piercing of tissue.

Figure 3:
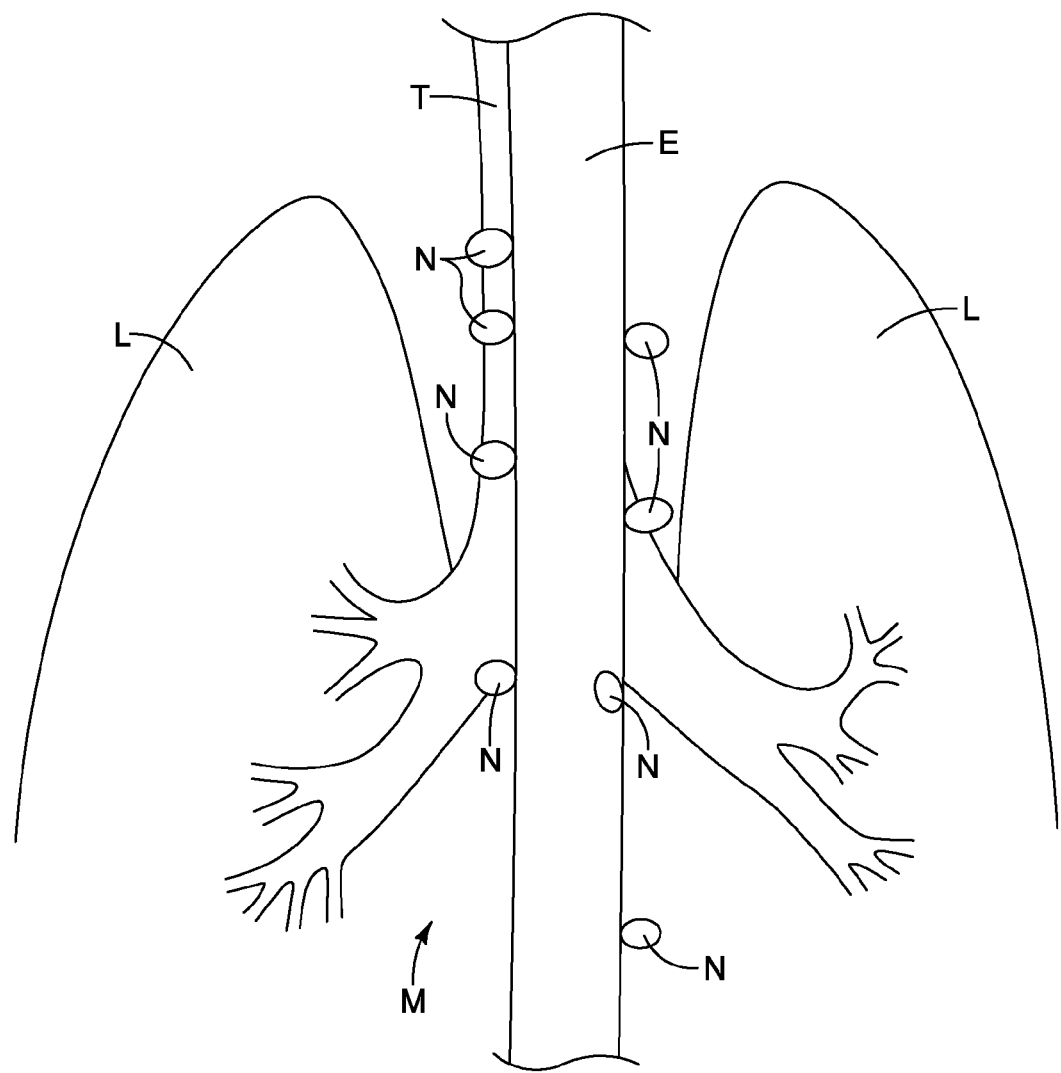
FIG. 3 is a schematic view illustrating a mediastinal cavity including lymph nodes.

Referring now to FIG. 3, the expandable device 20 described above may be used to capture, engage, and otherwise facilitate removal of a lymph node N from a bodily region, such as the mediastinal cavity M. In the exemplary method of FIGS. 4-12 described below, a selected lymph node N may be removed from the mediastinal cavity M via the esophagus E.

In FIG. 3, a patient's trachea T and lungs L are shown for reference purposes. Multiple mediastinal lymph nodes N are shown in FIG. 3, including an uppermost mediastinal node above the left brachial vein, upper paratracheal nodes above the aortic arch and below the left brachiocephalic vein, lower paratracheal nodes in the vicinity of the aortic arch and main bronchus, and a paraesophageal node below the aortic arch. In FIGS. 4-12, an enlarged illustration focuses on removal of the paraesophageal node below the aortic arch. However, any lymph node N, either situated within the mediastinal cavity or in another bodily passage, may be engaged or captured using the apparatus and methods described herein.

Figure 4:
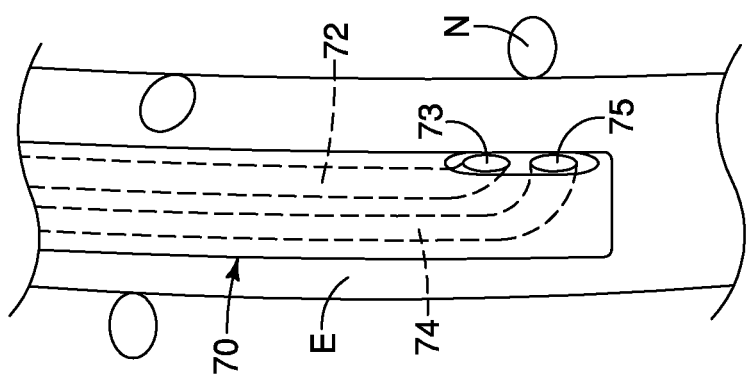

Referring to FIG. 4, in a first step, an endoscope 70 is maneuvered into a patient's mouth and down through the esophagus E. The endoscope 70 may comprise a dual-channel endoscope having first channel 72 and second channel 74. The first channel 72 may terminate at an exit port 73, while the second channel 74 may terminate at an exit port 75. While the lymph node procedure of FIGS. 4-12 may be performed using a single channel endoscope, it is preferred to utilize the multi-lumen endoscope 70.

The endoscope 70 may comprise an echo endoscope or other device suitable for imaging. When the endoscope 70 is positioned within the esophagus E, various lymph nodes N may be observed using ultrasound techniques. The endoscope 70 may be used to detect a node N suitable for treatment, such as a malignant node desired to be removed from the patient.

Figure 5:
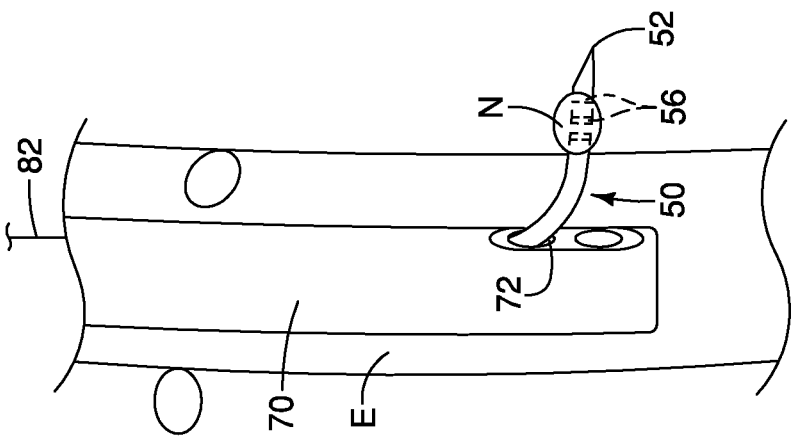

In a next step, after a suitable lymph node N had been detected, a first insertion tool 50 may be advanced distally through the first channel 72 of the endoscope 70 towards the target lymph node N. As shown in FIG. 5, the insertion tool 50 may be advanced distally through the exit port 73 of the endoscope 70 to pierce through the esophageal wall and through or around the target lymph node N. As noted above, the insertion tool 50 may comprise an EUS needle, such as the EchoTip® Ultrasound Needle, or the EchoTip® Ultran endoscopic Ultrasound Needle, both manufactured by Cook Endoscopy of Winston-Salem, N.C. The sharpened distal tip 52 of the insertion tool 50 facilitates piercing through the target lymph node N. The markers 56 of FIG. 2A may facilitate in determining how far the insertion tool 50 has penetrated into and through the esophageal wall and the target lymph node N. Alternatively, the insertion tool 50 may be advanced around the target lymph node N, instead of directly through the node. Preferably, the sharpened distal tip 52 is advanced just distal to the target lymph node N, as depicted in FIG. 5.

Figure 6:
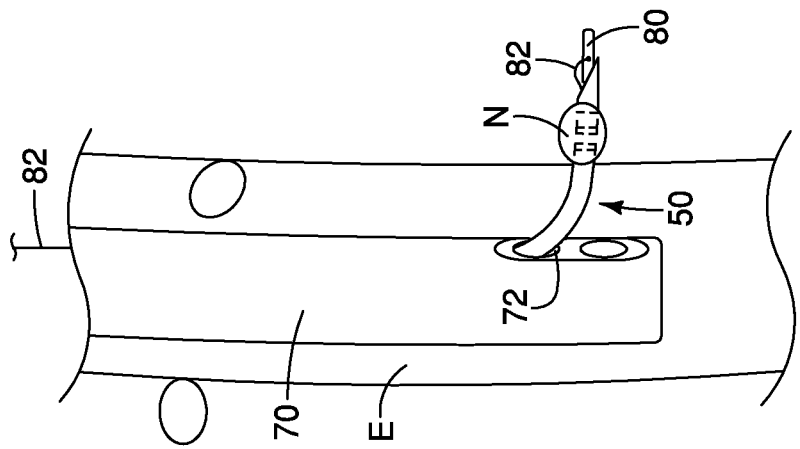
FIGS. 4-12 are exemplary method steps that may be used to remove a lymph node using the expandable device of FIGS. 1-2B.
Figure 7:
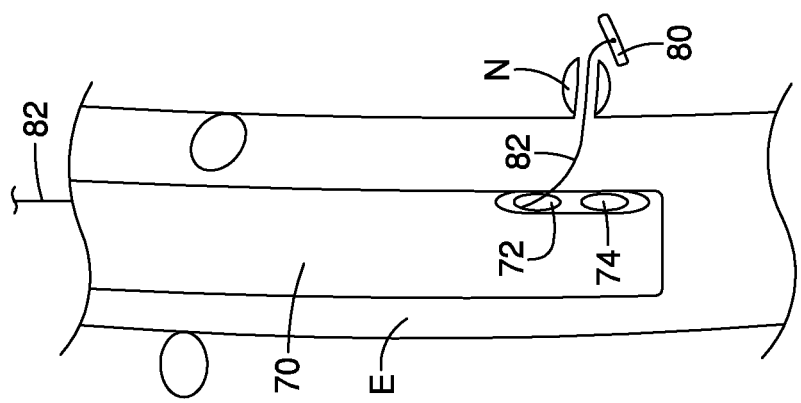

It should be noted that during advancement and placement of the insertion tool 50 beyond the target lymph node N, the hollow lumen 54 of the insertion tool 50 may be loaded with a visceral anchor or tissue anchor ("T-anchor") 80, which is coupled to a suture 82. The T-anchor 80 may be used for visceral wall stabilization, as explained in further detail below. As best seen in FIGS. 6-7, the T-anchor 80 may comprise a crossbar having first and second ends, wherein the suture 80 is coupled to a central region of the crossbar between the first and second ends. One exemplary configuration of a T-anchor suitable for use in the present embodiments is described in greater detail in U.S. Patent Publication No. 2008/0132948, which is hereby incorporated by reference in its entirety. Another example of a suitable visceral anchor is disclosed in U.S. Pat. No. 5,123,914, which also is hereby incorporated by reference in its entirety.

Referring still to FIGS. 6-7, with the insertion tool 50 disposed beyond the target lymph node N, the T-anchor 80 may be deployed. An inner stylet (not shown) may be disposed within the hollow lumen 54 of the insertion tool 50 at a location proximal to the T-anchor 80. The inner stylet then may be advanced distally, while the insertion tool 50 is held steady, in order to distally eject the T-anchor 80 from the hollow lumen 54, as depicted in FIG. 6. It should be noted that during delivery of the T-anchor 80, the suture 82 may be disposed within the hollow lumen 54 of the insertion tool 50, as depicted in FIG. 6, or alternatively may run along the outside of the insertion tool 50 within the first channel 72 of the endoscope 70.

After the T-anchor 80 is ejected from the insertion tool 50, the insertion tool 50 may be removed from within the first channel 72 of the endoscope 70. At this time, the T-anchor 80 is disposed just distal to the target lymph node N, with the suture 82 disposed through the lymph node N and extending proximally through the first channel 72 of the endoscope 70, as shown in FIG. 7. The proximal end of the suture 82 may be manipulated by a physician to aid in stabilization, i.e., when the suture 82 is pulled proximally the T-anchor 80 may be tilted into a transverse position and may be caught by the lymph node N.

Referring now to FIGS. 8-9, in a next step, the expandable device 20 of FIGS. 1-2B may be delivered and deployed to engage, capture or otherwise facilitate removal of the target lymph node N. In this example, the expandable device 20 is loaded into a second insertion tool, which is in the form of a catheter 90 having a proximal end 92 and a distal end 94. Alternatively, the expandable device 20 may be loaded through an insertion tool having a sharpened distal tip, such as an EUS needle similar to the insertion tool 50 described above. In a further alternative embodiment, the sheath member 58 described above, which may cover a sharpened insertion tool, may be used to deliver the expandable device in lieu of a separate catheter 90.

The catheter 90 has a lumen disposed between the proximal end 92 and the distal end 94. The expandable device 20 is loaded into the lumen of the catheter 90 in the delivery configuration shown in FIG. 2B. It should be noted that the catheter 90 may be advanced directly over the suture 82 of the T-anchor 80 towards the target lymph node N. Therefore, both the suture 82 and the expandable device 20, including the control member 30, may be simultaneously disposed within the lumen of the catheter 90, as depicted in FIGS. 8-9.

Alternatively, a proximal region of the suture 82 outside of the body, or a distal region of the suture 82 near the visceral wall of the esophagus E, may be cut off prior to insertion of the device carrying the expandable device 20. In this latter embodiment, if a new insertion device is used, such as a different endoscope, needle or catheter, to deliver the expandable device 20, then it may be advanced towards the visceral wall of the esophagus E without the need to be advanced directly over the suture 82 along its entire length.

As shown in FIG. 8, the catheter 90 may be advanced over the suture 82 and beyond the target lymph node N. Preferably, the proximal end of the suture 82 is tensioned while the catheter 90 is advanced distally beyond the esophageal wall and the target lymph node N, as depicted in FIG. 8. The tensioning of the suture 82 may retract the T-anchor 80 against the target lymph node N, which may facilitate stabilization of the node and advancement of the catheter 90 through the node. If necessary, the suture 82 can be locked into place to temporarily secure the tension and positioning the T-anchor 80. Without the stabilization via the T-anchor 80 and associated suture 82, the endoscope 70 may deflect away from the esophageal wall when the catheter 90 is advanced distally through the esophageal wall and lymph node N.

Referring to FIG. 9, after the distal end 94 of the catheter 90 has been advanced beyond the target lymph node N, the expandable device 20 may be deployed by advancing the control member 30 distally with respect to the endoscope 70. This causes the deployable members 45-47 of the expandable device 20 to extend distal to the distal end 94 of the catheter 90. When the deployable members 45-47 are no longer radially constrained by the catheter 90, they may assume their predetermined expanded configurations.

Figure 10:
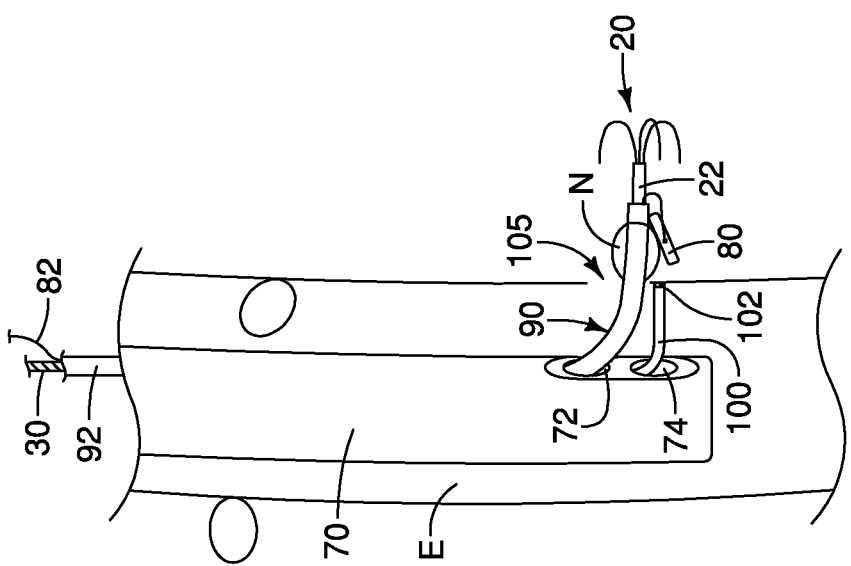

Referring to FIG. 10, a cutting device 100 may be used to enlarge the esophageal wall opening to facilitate extraction of the target lymph node N. The cutting device 100 may comprise a needle knife having an electrified cutting tip 102. The cutting device 100 may be advanced through the second channel 74 of the endoscope 70 towards the target site. An opening 105 may be carefully formed around the other components, including the catheter 90, as shown in FIG. 10. Optionally, the catheter 90 may be proximally retracted and removed prior to insertion or actuation of the cutting device 100.

Figure 11:
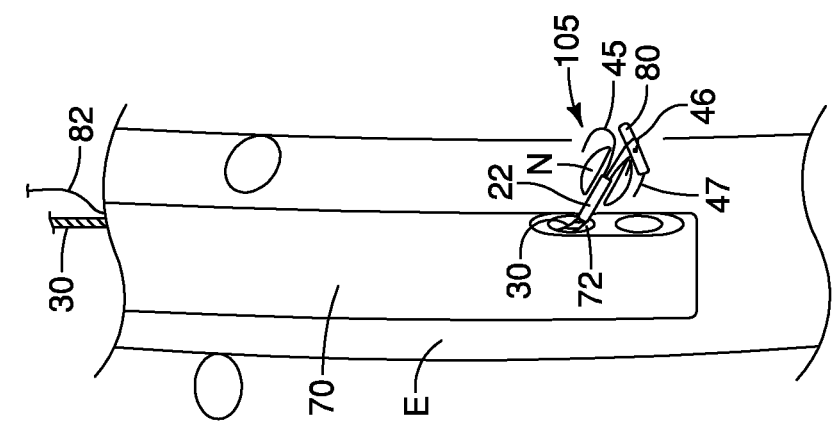

Referring to FIG. 11, in a next step, the expandable device 20 may be proximally retracted, by retracting the control member 30, to cause the deployable members 45-47 to engage, capture, or otherwise facilitate removal of the target lymph node N. In particular, the substantially 180-degree parachute-shaped configuration of the deployable members 45-47 may substantially or entirely surround the target lymph node N, then urge the target lymph node N in a proximal direction at least partially through the opening 105 and towards the lumen of the esophagus E. At about the same time, the suture 82 may be proximally retracted to retract the T-anchor 80 in harmony with the retraction of the target lymph node N and the expandable device 20.

Figure 12:
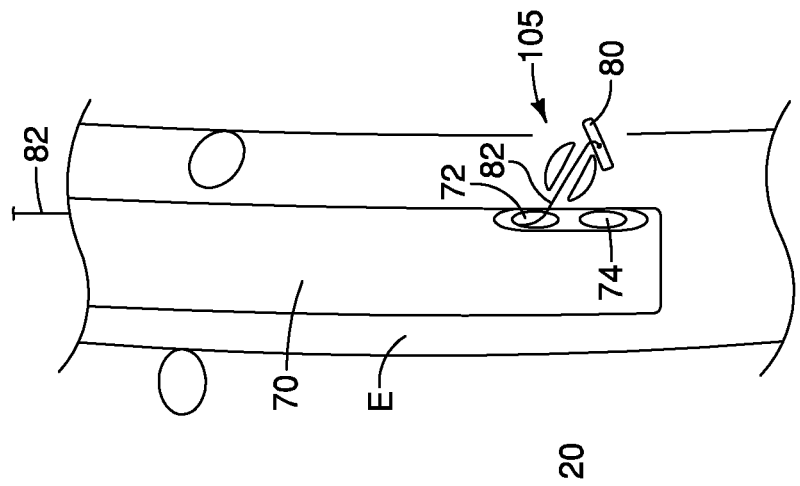

Referring to FIG. 12, in a next step, the expandable device 20 may be removed from engagement with the target lymph node N. In a first exemplary technique, the catheter 90 may be advanced distally over the deployable members 45-47, preferably while the T-anchor 80 is tensioned via the suture 82, to cause the deployable members 45-47 to assume the contracted configuration of FIG. 2B. The catheter 90 and control member 30 then may be proximally retracted to remove the expandable device 20 from engagement with the target lymph node N.

In a second exemplary technique, the deployable members 45-47 may pull through the target lymph node N and assume the retracted configuration of FIG. 2B when a predetermined force threshold is exceeded. In this example, the deployable members 45-47 will not retract when engaging and capturing the lymph node N, but may be configured to retract when a predetermined force threshold is exceeded, e.g., when the lymph node N is held in place against the catheter 90 and/or the endoscope 70. With the lymph node N held in place, further retraction of the control member 30 may force contraction of the deployable members 45-47 around or through the lymph node N and into the endoscope 70. In preliminary testing, the deployable members 45-47 may be contracted with a force in a range of about 0.5 pond to about 2.0 pond, although they may be tailored to contract upon any other suitable force.

At this time, the target lymph node N therefore is disposed partially or entirely within the esophagus E, with the suture 82 disposed through the lymph node N and the T-anchor 80 disposed distal to the lymph node N, as shown in FIG. 12. The cutting device 100 may be removed from the second channel 74 of the endoscope 70, and a removal device, such as a polypectomy snare, may be advanced through the second channel 74 and positioned to surround the target lymph node N. Electrocautery then may be used to cut the target lymph node N from the surrounding tissue. It should be noted that the suture 82 coupled to the T-anchor 80 also may be cut off by the removal device. The T-anchor 80 may be removed or may pass naturally through the body, while the remaining suture 82 may pulled through the first channel 72 of the endoscope 70.

In a final step, the visceral wall opening 105 created during the procedure may be closed using known techniques. As an example, the opening 105 may be closed using a suturing system by placing multiple anchors around the opening 105, then tensioning the sutures in a purse-string fashion. Alternatively, clips or other devices may be used to effect closure of the opening 105. The closure of the opening 105 may be performed through the first channel 72 and/or the second channel 74 of the endoscope 70, which then is removed from the patient's body.

While FIGS. 4-12 have illustrated the use of one expandable device 20 for engaging, capturing or otherwise facilitating removal of a lymph node N located within the mediastinal cavity, the expandable device 20 disclosed herein may be useful in many other procedures performed through the stomach or other visceral walls. Further, the order of the method steps shown in FIGS. 4-12 may be varied, or some of the steps may be omitted. For example, while the use of the T-anchor 80 may be used for stabilization of the visceral wall and/or lymph node throughout the procedure, the T-anchor 80 may optionally be omitted.

Further, it will be appreciated that while a dual-channel endoscope 70 has been shown for performing the procedure, a single channel endoscope or other suitable insertion apparatus may be used to deliver the components and perform the procedure described above. Similarly, two different endoscopes may be used in succession, for example, a first endoscope may be used to detect a suitable lymph node, advance an EUS needle and deploy the T-anchor 80, while a second endoscope may be advanced to the target site over the suture 82 of the T-anchor 80 and used to deploy the expandable device 20 and complete the procedure.

Further, it may be desirable to only use the insertion tool 50 to deliver both the T-anchor 80 coupled to the suture 82 and the expandable device 20 coupled to the control member 30, without exchanging the insertion tool 50. In this example, the T-anchor 80 may be loaded within the hollow lumen 54 of the insertion tool 50 at a location distal to the deployable members 45-47. The suture 82 and the control member 30 may extend adjacent to one another within the hollow lumen 54. In use, distal advancement of the control member 30 may cause the deployable members 45-47 to be distally advanced to initially eject the T-anchor 80 from the distal end of the insertion tool 50, for purposes described above. Then, at a subsequent desired time, the deployable members 45-47 may be ejected from the insertion tool 50. In this example, therefore, only one insertion tool 50 is used and does not need to be exchanged.

Referring now to FIGS. 13-14, in an alternative embodiment, the expandable device 20 may be adapted to anchor into a visceral wall and/or other tissue to facilitate stabilization during a translumenal procedure using the dual-channel endoscope 70. In a first method step, an insertion tool 50, such as an EUS needle, is distally advanced through the first channel 72 of the endoscope 70 and pierces through the esophageal or other visceral wall, as generally set forth above. In this embodiment, the hollow inner lumen 54 of the insertion tool 50 may be loaded with the expandable device 20. Upon desired placement of the insertion tool 50, the control member 30 coupled to the expandable device 20 is advanced distally with respect to the insertion tool 50. This causes the deployable members 45-47 of the expandable device 20 to extend distal to the insertion tool 50 and assume their predetermined expanded configurations, as shown in FIG. 13.

The insertion tool 70 then may be retracted into the first channel 72 of the endoscope 50, and the deployable members 45-47 then may be retracted proximally by retraction of the control member 30. This causes the deployable members 45-47 of the expandable device 20 to engage, penetrate, abut or otherwise anchor into an outer portion 107 of the visceral wall. While a translumenal procedure is shown performed through the esophagus, other visceral wall, such as the stomach wall, may be perforated.

Such anchoring by the deployable members 45-47 of the expandable device 20 promotes stabilization of the system when additional components are advanced, or procedures performed, through the first channel 72 and/or the second channel 74 of the endoscope 70. The expandable device 20 also may reduce the likelihood of the endoscope 70 deflecting away from the visceral wall as other components are advanced distally from the endoscope 70.

For example, in the case of lymph node removal, a first expandable device 20 may be deployed through the first channel 72 to help stabilize the system, and then a second expandable device 20 may be deployed through the second channel 74 to facilitate removal of the lymph node, as described above. In this case, the first expandable device 20 may stabilize the endoscope 70 while the lymph node is cut and closing devices, such as anchors, are placed for closing the opening in the visceral wall.

Upon completion of the procedure, further retraction of the control member 30 may cause the deployable members 45-47 to pull through the visceral wall and assume the retracted configuration, shown in FIG. 2B, within the first channel 72 of the endoscope 70. As noted above, the deployable members 45-47 may assume the retracted configuration by advancing the insertion device 50 or catheter 90 distally, or it may pull through the visceral wall and assume the retracted configuration of FIG. 2B when a predetermined force threshold is exceeded. Subsequently, any visceral wall openings formed during the procedure may be closed using known techniques, for example, purse-string suturing or clipping.

Figure 16:
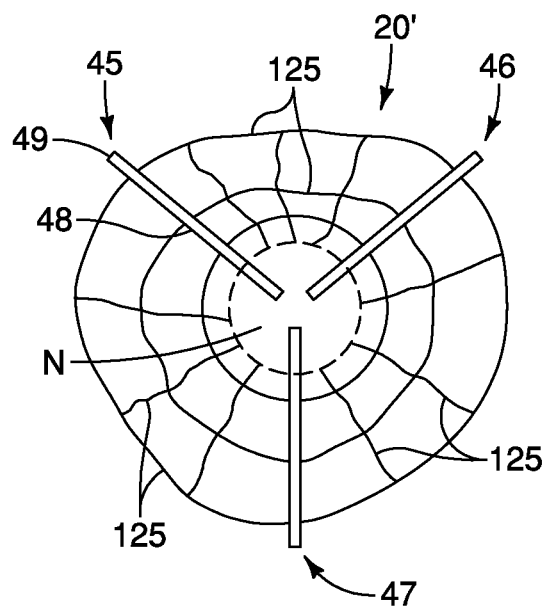
FIG. 16 is an end view of a lymph node and an alternative expandable device in a deployed state.

Referring now to FIG. 16, in an alternative embodiment, an expandable device 20' comprises an additional capture member 125. The capture member 125 may comprise one or more wires coupled to the deployable members 45-47, for example, in the form of a flexible and expandable netting disposed between the deployable members 45-47, to facilitate engagement with and removal of a lymph node upon retraction of the expandable device 20'. The capture member 125 may be soldered or welded to selected regions along the deployable members 45-47, e.g., in the vicinity of the respective apices 48 and distal tips 49.

Figure 17A:
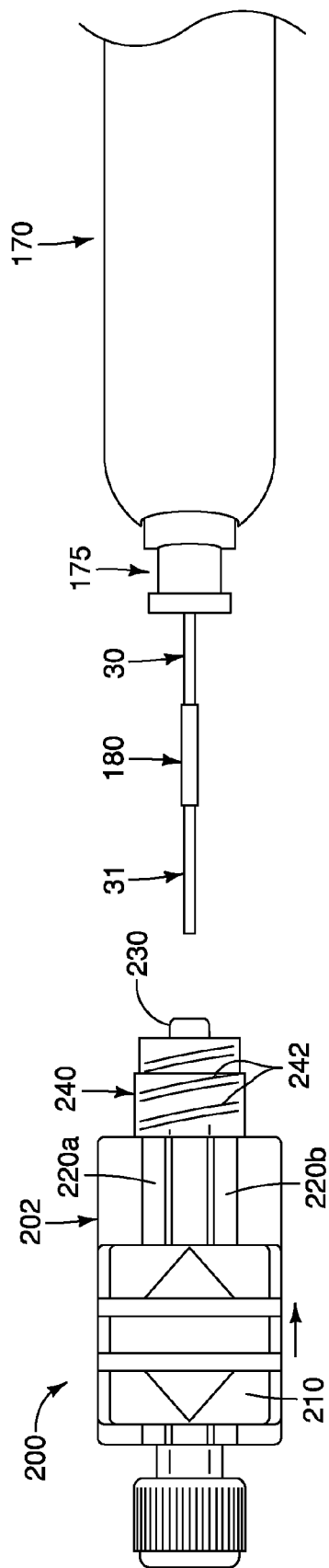
FIGS. 17A-17B are side schematic views of a control assembly that may be remvoably coupled to a handle, as shown in uncoupled and coupled states, respectively.

Referring now to FIGS. 17-19, a control assembly 200 that may be removably coupled to a handle 170 is described. In FIG. 17A, a proximal region 31 of the control member 30, which as described above may be coupled to deployable members 45-47, extends proximally from the handle 170. The handle 170 may be coupled to the proximal end of the insertion tool 50 described above, and the control member 30 may extend through the hollow lumen 54 of the insertion tool 50, as explained above.

Figure 17B:
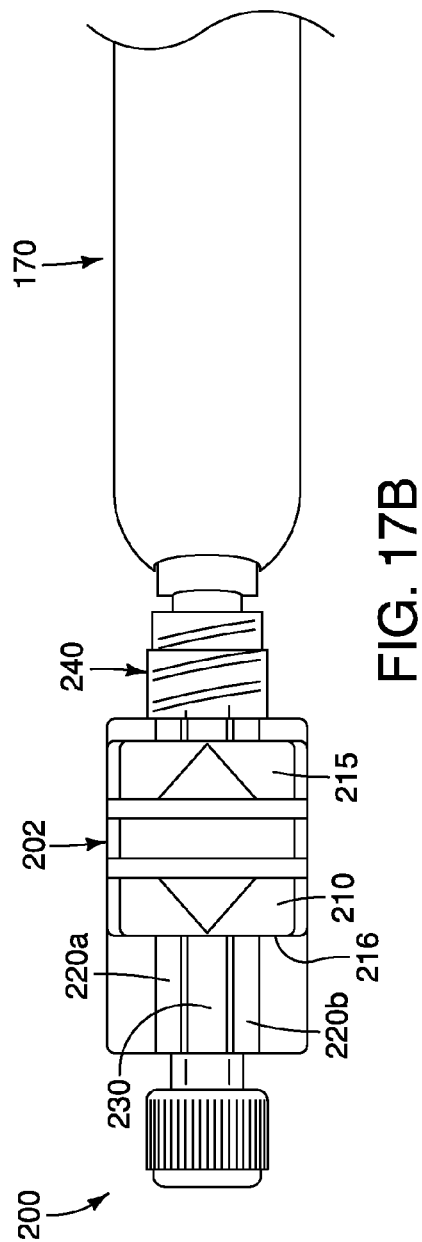

The control assembly 200 generally comprises a platform 202 having guide elements 220a and 220b, which may be in the form of longitudinally-oriented tracks. The guide elements 220a and 220b guide longitudinal movement of a slidable actuator 210 between unlocked and locked states, as shown in FIGS. 17A-17B, respectively. As shown in FIG. 19, a surface of the slidable actuator 210 comprises grooves 212a and 212b, which are configured to securely slide along the guide elements 220a and 220b of the platform 202.

The control assembly 200 further comprises tubing 230 extending between the guide elements 220a and 220b along at least a portion of its length. As shown in FIGS. 18A-18B, the tubing 230 may comprise a lateral bore 233 formed therein, which is generally sized to receive a stopper 250. Notably, in FIGS. 18A-18B, the slidable actuator 210 has been removed from the platform 202 for illustrative purposes, while in FIG. 18B, the stopper 250 has been removed from the bore 233 of the tubing 230 for illustrative purposes.

The control assembly 200 further comprises an engaging region 240, which may partially surround the tubing 230, as shown in FIG. 17A. The engaging region 240 of the control assembly 200 may engage a proximal region 175 of the handle 170, as shown in FIG. 17B. For example, threading 242 on the engaging region 240 may engage complementary threading (not shown) on the proximal region 175 of the handle 170.

When the control assembly 200 is unattached to the handle 170, as shown in FIG. 17A, an exchange of components may take place. For example, after the deployable members 45-47 coupled to the control member 30 have engaged a lymph node or other tissue, as explained above, the insertion tool coupled to the handle 170 may be proximally removed over the length of the control member 30. Subsequently, another insertion tool may be distally advanced over the control member 30, while the control member 30 and the deployable members 45-47 remain engaged with the lymph node or other tissue.

If it becomes desirable to proximally advance or retract the control member 30, and thus the deployable members 45-47, along with the handle 170, then the control assembly 200 is coupled to the handle 170 as shown in FIG. 17B. The slidable actuator 210 then is distally advanced along the guide elements 220a and 220b, as described above. Notably, the slidable actuator has a distal end 215 having a relatively deep recess, which tapers to a relatively shallow recess at a proximal end 216, as shown in FIG. 19. Thus, with distal advancement of the slidable actuator 210, a shallower region of the slidable actuator 210 begins to cover the stopper 250, and the underside of the slidable actuator 210 progressively engages the stopper 250. The slidable actuator 210 therefore urges the stopper 250 radially inward in the position shown in FIG. 17B, and the stopper 250 presses radially inward upon the tubing 230. Since the proximal region 31 of the control member 30 is disposed within the tubing 230, inward compression of the tubing 230, via the stopper 250, pinches upon the control member 30. In this state, the control assembly 200 securely grasps the proximal region 31 of the control member 30 positioned adjacent to the bore 233. Optionally, a cannula 180 may be soldered or otherwise secured to the proximal region 31 of the control member 30 to provide a locally increased profile that may facilitate grasping of the control member 30 by pinching of the tubing 230. When it is desired to remove the handle 170 and insertion tool again, the slidable actuator 210 is moved back proximally to the state of FIG. 17A, thus releasing the stopper 250 and the engagement of the tubing 230 with the control member 30.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A method for facilitating removal of a lymph node, the method comprising:
    providing an expandable device comprising at least one deployable member having contracted and expanded states;
    advancing at least a portion of the expandable device beyond the lymph node with the deployable member in the contracted state;
    deploying the deployable member at a location distal to the lymph node, wherein the deployable member begins to deploy distal to the distal end of the lymph node, and wherein the deployable member, in the expanded state, comprises a configuration sized to at least partially circumferentially surround the lymph node; and
    proximally retracting the expandable device to cause the deployable member to engage the lymph node.

2. The method of claim 1 wherein advancing at least a portion of the expandable device through the lymph node further comprises:
    advancing an insertion tool through the lymph node, wherein the insertion tool comprises a hollow lumen, and wherein the expandable device is disposed within the hollow lumen with the deployable member in the contracted state; and
    advancing the deployable member distal to the insertion tool to cause the deployable member to expand.

3. The method of claim 2 wherein the deployable member self-expands into a parachute-shaped configuration in the expanded state when no longer constrained by the insertion tool.

4. The method of claim 1 further comprising:
    providing a T-anchor coupled to a suture, wherein the T-anchor is disposed within a hollow lumen of an insertion tool;
    advancing the insertion tool distally beyond the lymph node;
    ejecting the T-anchor from the insertion tool at a location distal to the lymph node; and
    retracting the suture to cause the T-anchor to engage the lymph node and promote stabilization of the lymph node.

5. The method of claim 4, further comprising:
    removing the insertion tool from within the lymph node;
    providing a catheter having a lumen, wherein the expandable device is disposed for delivery within the lumen of the catheter; and
    distally advancing the catheter through the lymph node while tensioning the suture to stabilize the lymph node.

6. The method of claim 1, wherein the lymph node is removed translumenally through a visceral wall, the method further comprising:
   creating an opening in the visceral wall to facilitate removal of the lymph node,
   engaging the lymph node with the expandable device and retracting the expandable device to move the lymph node in a proximal direction through the visceral wall.

* * * * *